(12) United States Patent
Wang et al.

(10) Patent No.: US 9,731,076 B2
(45) Date of Patent: Aug. 15, 2017

(54) MULTI-COMPARTMENT PRE-FILLED MIXING SYRINGES WITH BYPASS

(75) Inventors: Yi-Lan Wang, Belle Mead, NJ (US); Leo B. Kriksunov, Ithaca, NY (US)

(73) Assignee: Ethicon, Inc., Somerville, NJ (US)

(*) Notice: Subject to any disclaimer, the term of this patent is extended or adjusted under 35 U.S.C. 154(b) by 1127 days.

(21) Appl. No.: 13/537,202

(22) Filed: Jun. 29, 2012

(65) Prior Publication Data
US 2014/0005636 A1    Jan. 2, 2014

(51) Int. Cl.
*A61M 5/28* (2006.01)
*A61M 5/315* (2006.01)
*A61M 5/31* (2006.01)

(52) U.S. Cl.
CPC .......... *A61M 5/284* (2013.01); *A61M 5/3129* (2013.01); *A61M 5/31511* (2013.01)

(58) Field of Classification Search
CPC . A61M 5/284; A61M 5/3129; A61M 5/31511
See application file for complete search history.

(56) References Cited

U.S. PATENT DOCUMENTS

| | | | |
|---|---|---|---|
| 2,549,417 A * | 4/1951 | Brown | A61M 5/2448 206/221 |
| 3,511,239 A | 5/1970 | Tuschhoff | |
| 3,662,753 A | 5/1972 | Tassell | |
| 3,766,917 A | 10/1973 | Wimmer | |
| 3,985,122 A | 10/1976 | Topham | |
| 4,036,225 A | 7/1977 | Maury | |
| 4,226,236 A * | 10/1980 | Genese | A61M 5/284 604/125 |
| 4,424,057 A | 1/1984 | House | |
| 4,613,326 A | 9/1986 | Szware | |
| 5,080,649 A * | 1/1992 | Vetter | A61M 5/31596 604/191 |
| 5,364,350 A * | 11/1994 | Dittmann | A61K 9/0019 604/416 |
| 5,637,100 A | 6/1997 | Sudo | |

(Continued)

FOREIGN PATENT DOCUMENTS

| | | |
|---|---|---|
| EP | 242956 | 10/1987 |
| WO | 03084840 | 10/2003 |

(Continued)

OTHER PUBLICATIONS

International Preliminary Report on Patentability re: PCT/US2013/046566 dated Dec. 31, 2014.

(Continued)

*Primary Examiner* — Emily Schmidt
*Assistant Examiner* — Lauren M Peng
(74) *Attorney, Agent, or Firm* — Leo B. Kriksunov

(57) ABSTRACT

The present invention is directed to a multi-compartment medical device for segregated storage and on demand mixing of at least two components and expression of a resulting mixture from the device having a tubular barrel with an opening and a gasket sealing the rear end through which a plunger is axially slidable within the tubular barrel. At least one bypass is provided in the barrel in order to enable fluid movement of the components between front and rear compartments and rear compartments. The present invention is also directed to methods for the use of such devices.

2 Claims, 10 Drawing Sheets

(56) References Cited

U.S. PATENT DOCUMENTS

| | | | |
|---|---|---|---|
| 5,704,918 A | | 1/1998 | Higashikawa |
| 5,785,683 A | * | 7/1998 | Szapiro ................ A61M 5/284 |
| | | | 604/228 |
| 5,817,056 A | | 10/1998 | Tanaka et al. |
| 5,899,881 A | | 5/1999 | Grimard et al. |
| 5,971,953 A | * | 10/1999 | Bachynsky ........... A61M 5/284 |
| | | | 604/181 |
| 6,419,656 B1 | | 7/2002 | Vetter et al. |
| 6,817,987 B2 | | 11/2004 | Vetter et al. |
| 7,021,561 B2 | | 4/2006 | Vedrine et al. |
| 7,731,678 B2 | | 6/2010 | Tennican et al. |
| 2003/0187388 A1 | | 10/2003 | Sharon et al. |
| 2008/0275387 A1 | | 11/2008 | Yeadon et al. |
| 2011/0155620 A1 | | 6/2011 | Kuu |

FOREIGN PATENT DOCUMENTS

| | | |
|---|---|---|
| WO | 2006003653 | 1/2006 |
| WO | WO 2007/034020 | 3/2007 |
| WO | 2008150208 | 12/2008 |
| WO | WO 2011/076852 | 6/2011 |

OTHER PUBLICATIONS

International Search Report re: PCT/US2013/046566 dated Oct. 16, 2013.
Supplementary European Search Report re: EP13809108 dated Feb. 26, 2016.

* cited by examiner

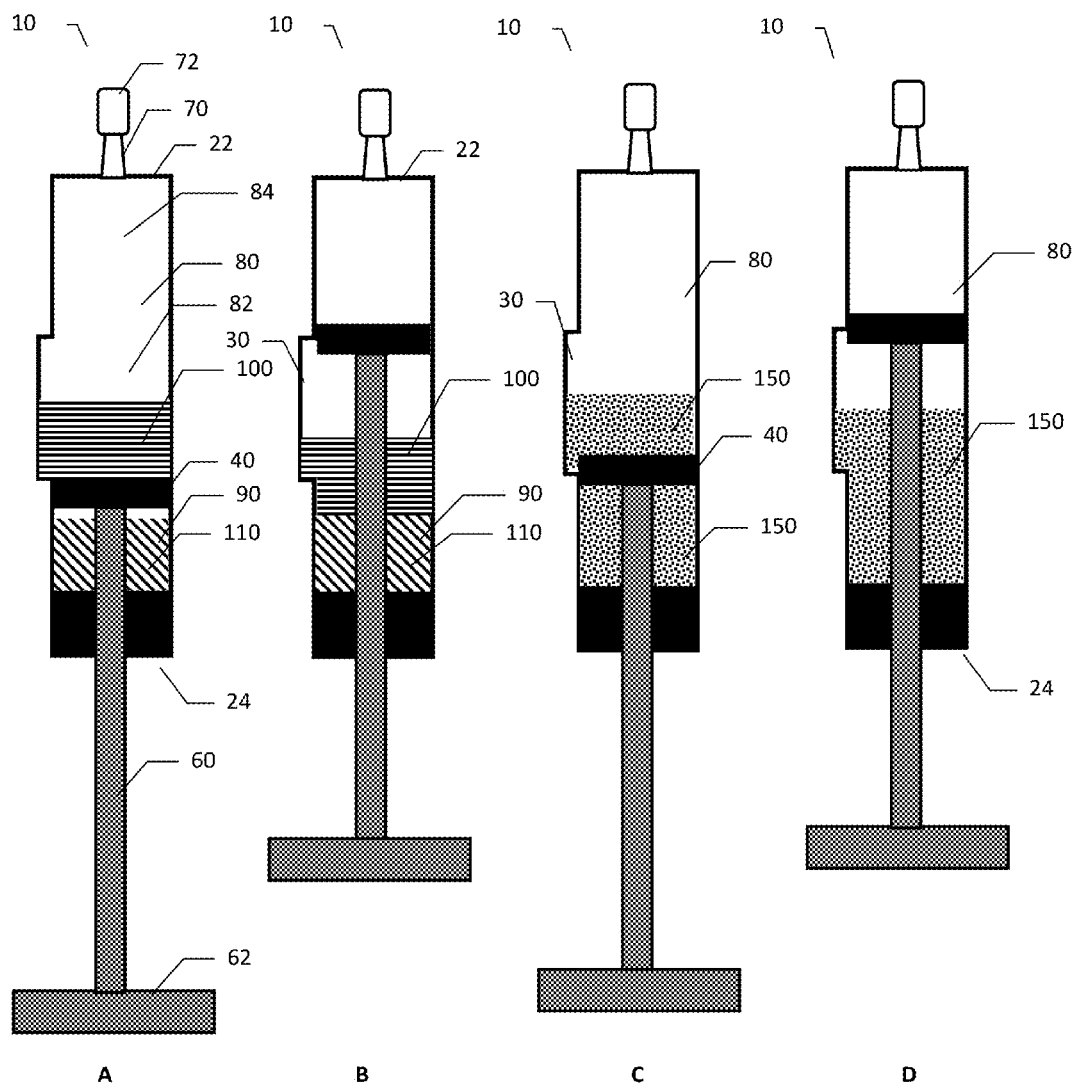
FIGURE 3A-D

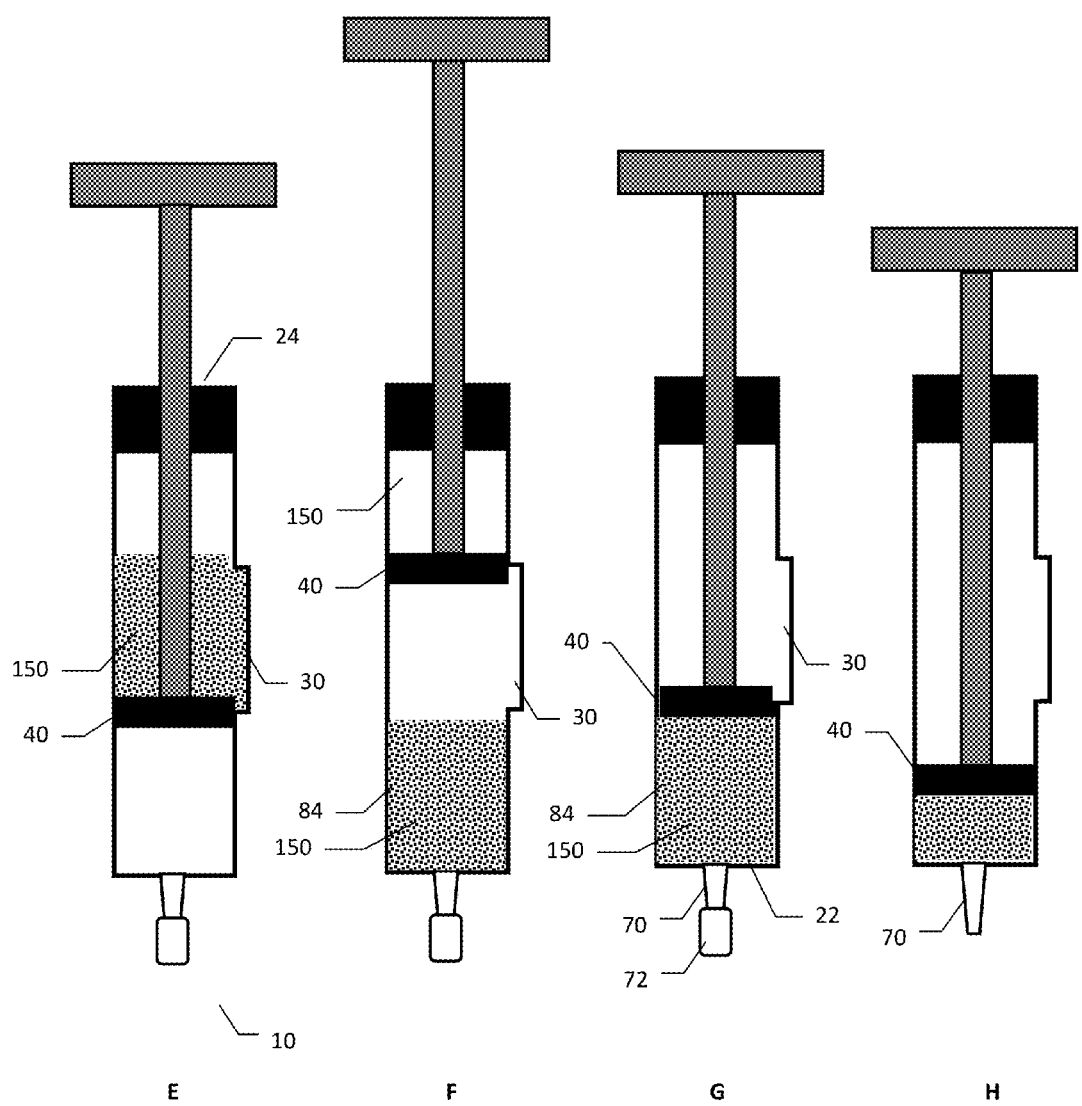
FIGURE 3 E-H

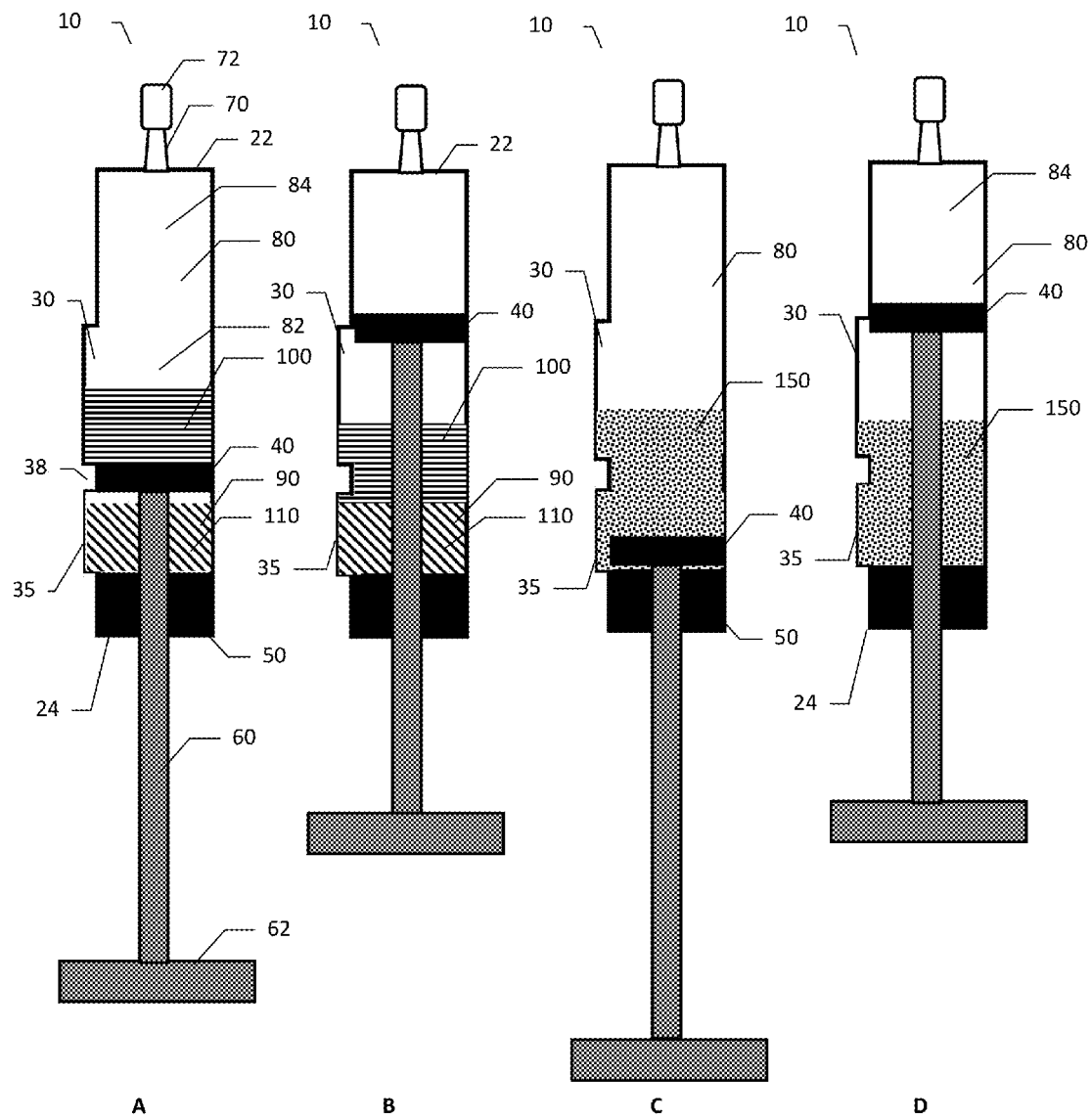

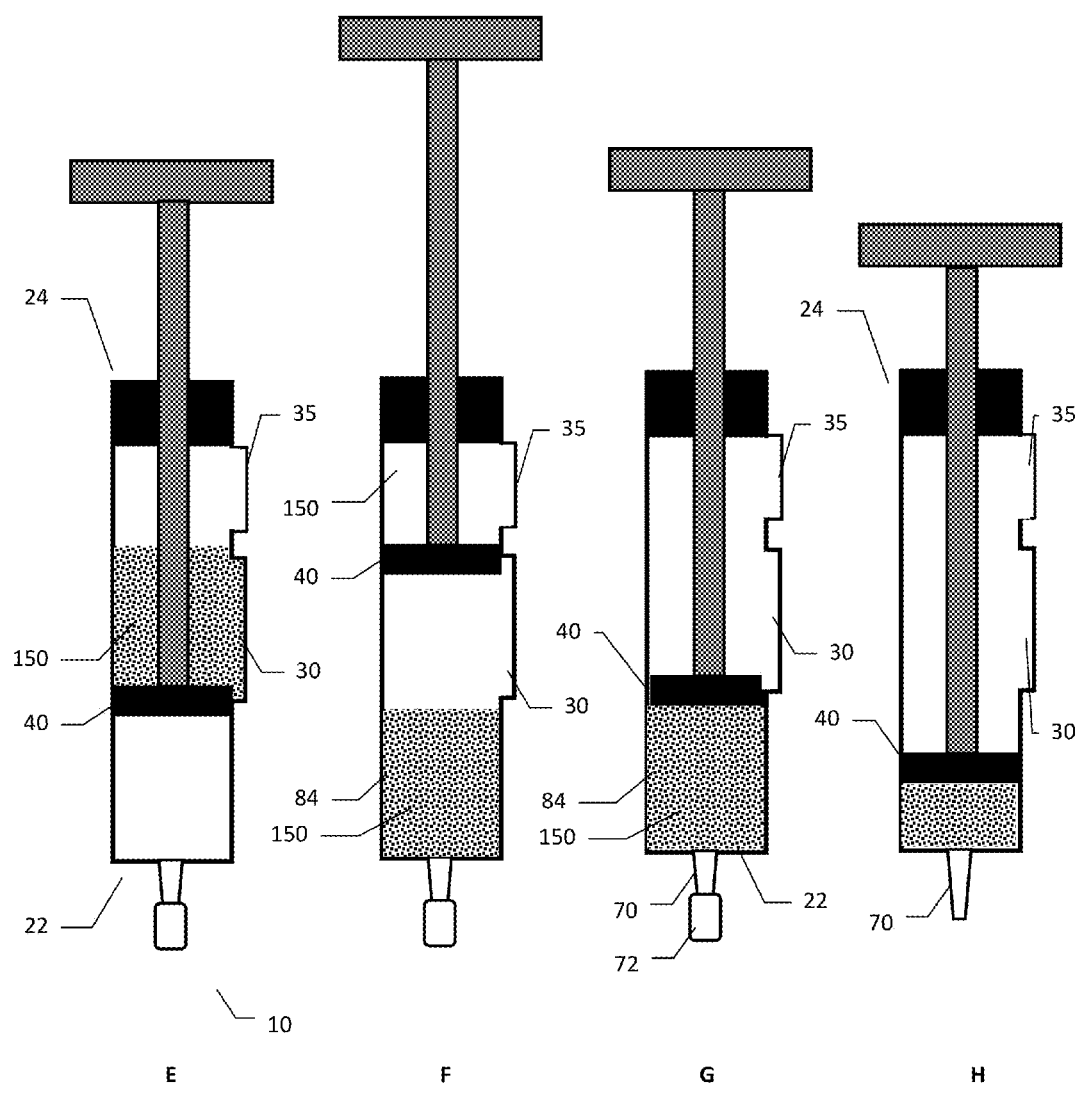

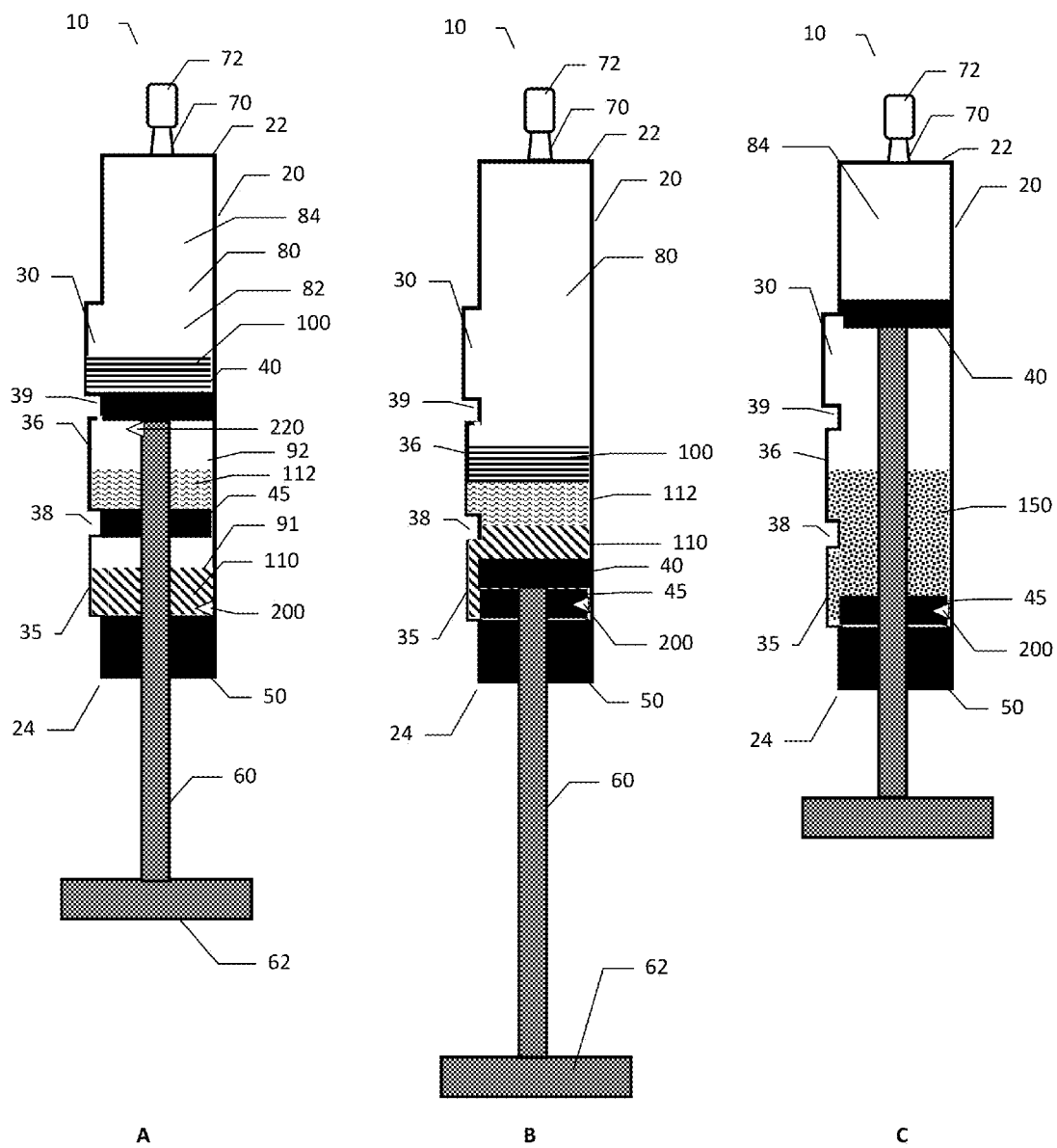

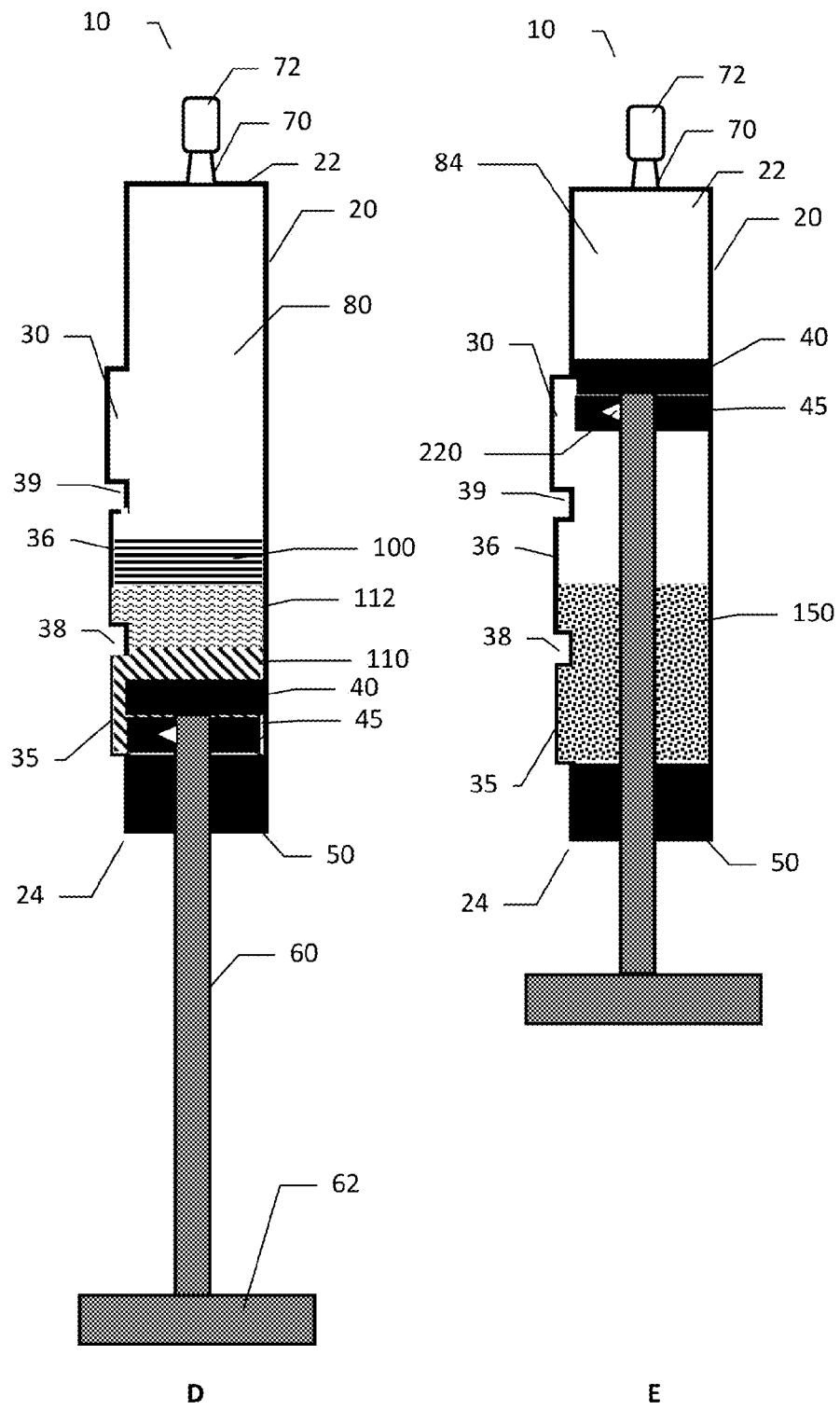

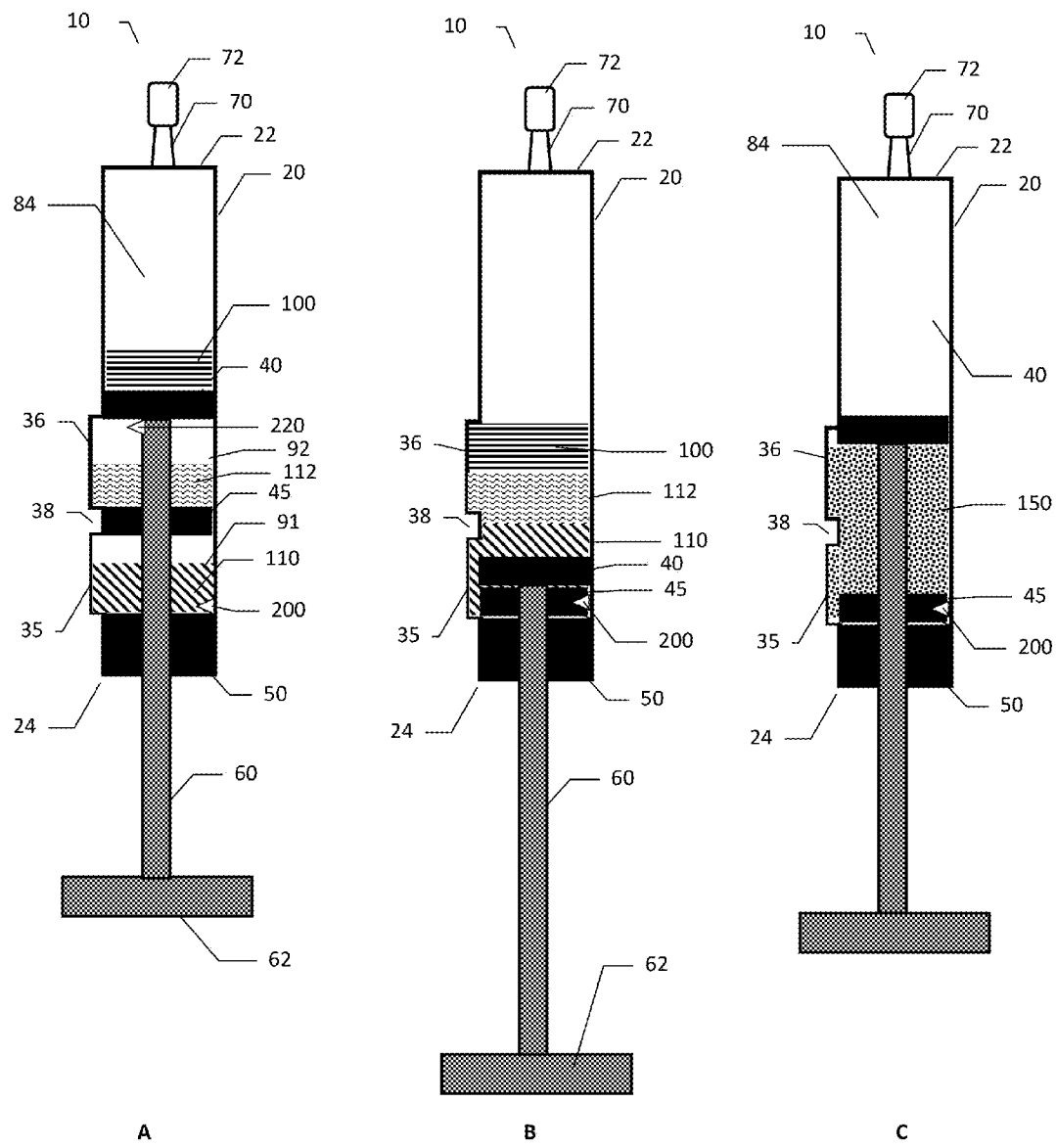

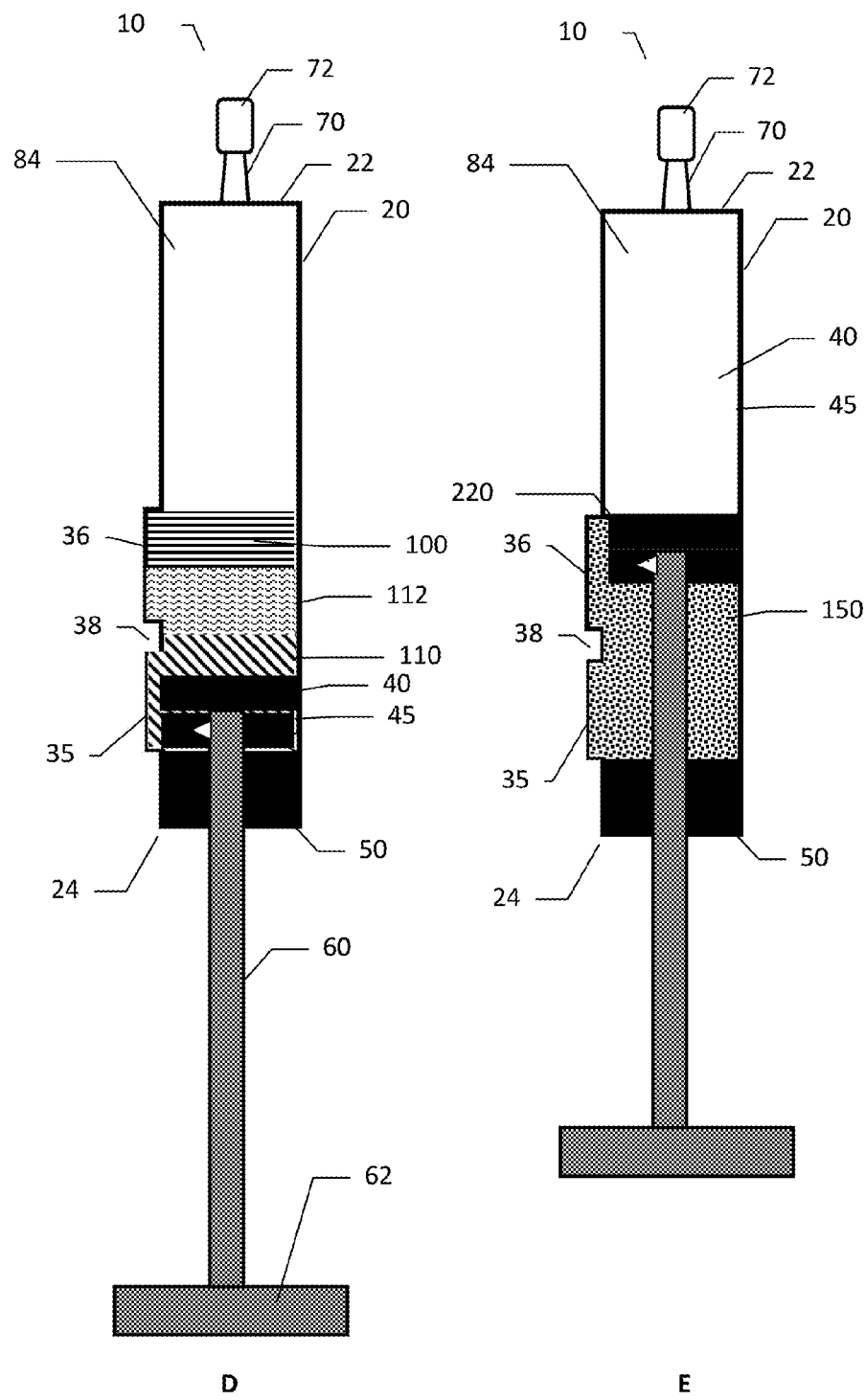
FIGURE 6 D-E

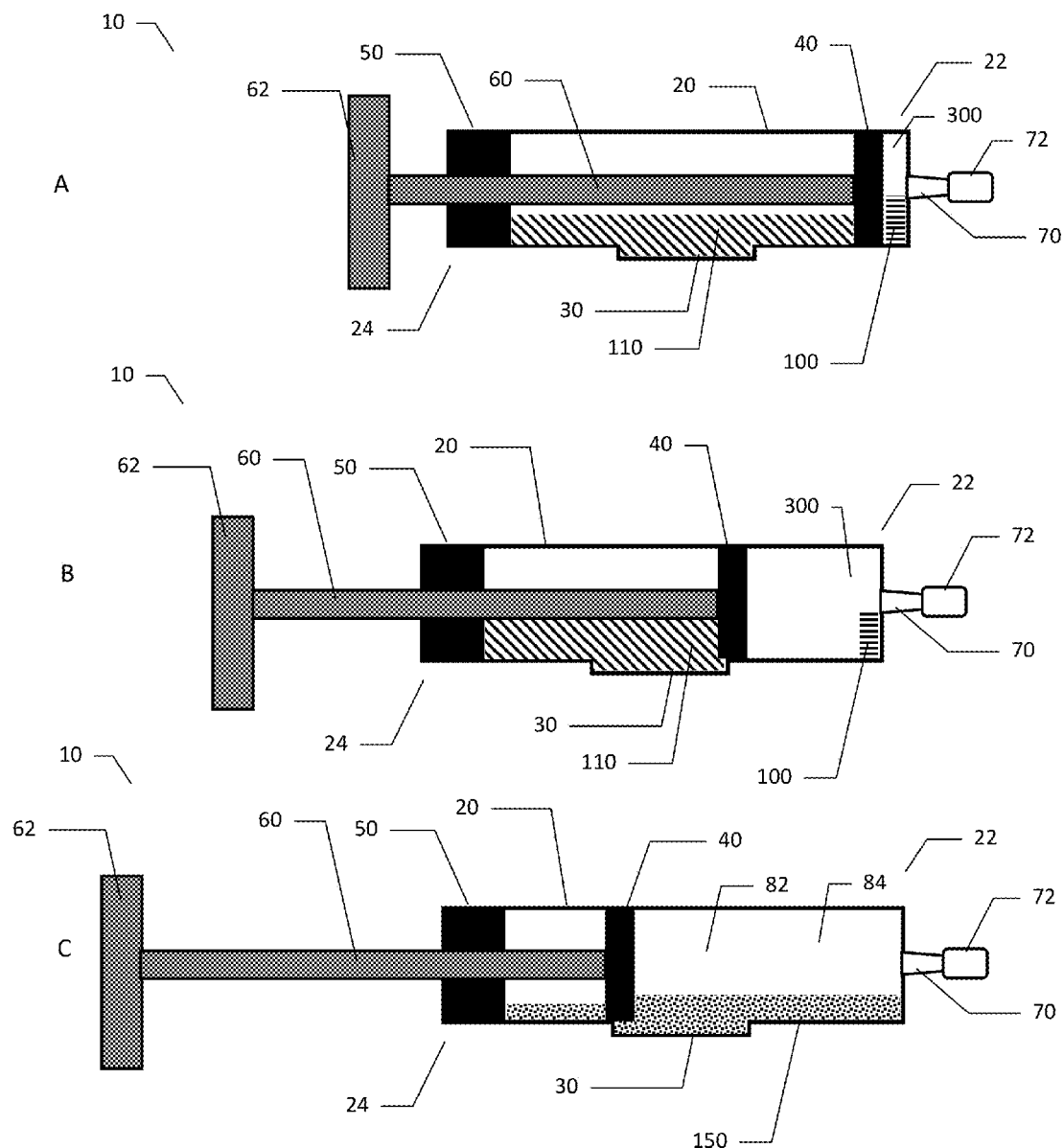

MULTI-COMPARTMENT PRE-FILLED MIXING SYRINGES WITH BYPASS

FIELD OF THE INVENTION

The present invention relates to multi-compartment medical devices for segregated storage and on demand mixing of at least two components and for expressing the resulting mixture from the device for use in treating a patient. The invention further relates to methods of segregated storage and on demand mixing of at least two components and for expressing the resulting mixture from the device. The invention further relates to devices for and methods of reconstituting lyophilized materials.

BACKGROUND OF THE INVENTION

Currently there are a number of biomedical applications where there is a need to rapidly and thoroughly mix two or more components in the operating room substantially immediately prior to administration to the patient. The mixing of components can typically involve extraction of one component in fluid form from a vial or other container and transfer of such component into a separate container which holds another component. In particular instances, only a portion of the contents of a vial or container is to be utilized for preparing a mixture prior to administering. Accordingly, the extraction and transfer can involve precise measuring of one or more components to be mixed.

A variety of problems may occur when utilizing conventional methodology and devices for mixing and/or administering biomedical agents to an individual. For example, where multiple components are to be mixed, extraction and transfer of one component and introduction of such component into another component can potentially expose one or both of the components to a non-sterile or contaminated environment leading to contamination of the resulting mixture. Additionally, incomplete extraction or improper measurement of one or more components can result in preparation and/or administration of an improper dosage. In particular instances, once biomedical agents are mixed the mixture must again be extracted from a vial or container into a syringe prior to administering to an individual. Such additional transfer can lead to additional opportunities for contamination, incomplete extraction of contents and/or inaccurate measuring of a component or the resulting biomedical agent. In practice, there is limited availability of sterile environments for maintaining sterility during transfer and/or mixing of components, or preparation and transfer of biomedical agents. Additional errors can result from use of the wrong diluent to reconstitute the medication. Finally, preparation of biomedical agents utilizing multiple components can be tedious and time consuming due to factors such as the need to access individually packaged items such as separate vials and/or transfer devices, or to measure one or more components to be combined to form the biomedical agent. The multiple packaging and storage containers such as separate vials and/or transfer devices increase the cost of care and also create an additional waste stream which has to be dealt with in accordance with regulations governing the disposal of biomedical waste. There is a need in a simplified system for segregated storage and rapid and thorough mixing of two or more components in the operating room substantially immediately prior to administration to the patient, which can also reduce the risk of contamination during preparation.

Preparation of injectable drugs or hemostatic agents often requires a thorough mixing of two or more components which are stored in separate compartments. Use of multiple vials and syringes is expensive and wasteful, complicates the preparation, increases the probability of error, and requires proper disposal of used containers. For example, in preparation of a hemostatic paste based on biopolymer, such as gelatin, in mixture with thrombin, the surgeon often performs the mixing by using two interconnected connected syringes and moving the paste back and forth to mix gelatin with saline solution containing thrombin. One syringe is then discarded.

In preparation of reconstituted solution of a protein, such as reconstituted thrombin or fibrinogen from lyophilized thrombin or fibrinogen, the dry lyophilized powders need to be thoroughly mixed when reconstituted with water or saline.

In some commercially available hemostatic kits, reconstitution of lyophilized thrombin is performed in a vial into which water is injected from a syringe. After swirling the mixture, the solution is aspirated back into syringe. The reconstitution of the thrombin can be slow because there is no forced mixing in the vial. Then the solution is expressed into a sterile cup and the syringe and the vial are discarded. The solution is then aspirated by another syringe can be connected via a luer to the syringe containing the gelatin matrix. The contents are then mixed by moving between syringes back and forth, after which one syringe is discarded and the ready mixture is expressed from the last syringe. The process of using and discarding a vial, a cup, and two syringes to prepare one syringe with the hemostatic paste in multiple sequential steps requires time and high attentiveness of the healthcare professional.

There are a number of known multi-chamber, single barrel as well as multi-barrel syringes which attempt to accomplish the segregated storage of two components and subsequent mixing and expression of the resulting mixture from the syringe.

A number of references are utilizing an intermediate free piston or stopper in front of the plunger separating the two sub-compartments and a bypass channel or groove in the sidewall of the syringe barrel.

Other references describe the plunger separating front compartment and back compartment in the barrel of the syringe, with a one way valve in the plunger enabling mixing of the materials in the two compartments.

Other references disclose a secondary barrel coaxially located within the first barrel, wherein the second barrel might be used as a plunger or plunger stem.

Other references disclose two syringes which are interconnected and used for mixing components by moving from the mix from one syringe to another.

None of the references provide, in a single syringe, for the capability of vigorous back and forth mixing between the compartments and thus for rapid effective reconstitution and/or mixing of separately stored components. The known systems utilizing valves are complex and can plug up with the mixing materials, or can leak during storage. Only uni-directional movement of the plunger (i.e. forward) is possible, resulting in insufficiently efficient mixing of the components.

U.S. Pat. No. 6,817,987 titled "Mixing Hypodermic Syringe" discloses a syringe holding both a solvent and a soluble component having a tubular body with a bypass, a plunger axially slidable in the tubular body, and a stem projecting axially rearward out of the body from the plunger. A cover fits over the front end of the tubular body and is so tight that the front compartment can be pressurized to a superatmospheric pressure without leakage out the front end. A free piston slidable in the tubular body forward of the plunger subdivides the body forward of the plunger into a front compartment at the front body end holding the soluble component and a rear compartment between the plunger and the piston and holding the solvent. Stops are provided for arresting the free piston when it is level with the bypass in a position permitting flow through the bypass between the compartments.

U.S. Pat. No. 5,080,649 titled "Dual-Compartment Hypodermic Syringe" discloses a hypodermic syringe that has an elongated tubular body having a front end adapted to carry a needle, a rear end, and a bypass between the ends. A front partition piston defines with the front end a front compartment that is adapted to hold a substance and a rear piston defines with the front partition piston a rear compartment adapted to hold a fluid miscible with the front-compartment substance. The front partition piston is displaceable into a middle position in the bypass for fluid communication between the compartments. A stem projecting rearward out of the body from the rear piston is provided with axially spaced front and rear external screwthreads and has a clear region between the screwthreads. A damper on the rear end of the body can engage the screwthreads for slowing axial movement of the screwthreads past the rear end of the body and for permitting relatively rapid axial movement of the stem in the body when the clear region is level with the damper.

U.S. Pat. No. 6,419,656 titled "Medical Syringe with Braked Step-Advance Plunger" discloses a medical syringe that has a tubular body extending along an axis and having a front end and a rear end, a plunger axially slidable in the body and carrying a stem projecting axially rearward out of the body from the plunger, and a free piston slidable in the body forward of the plunger and subdividing the body forward of the plunger into a front compartment at the front body end and a rear compartment between the plunger and the piston. The body is formed with a bypass passage forward of the piston in a starting position so the front compartment can hold a soluble medicament and the rear compartment can hold its solvent. Structure at the rear body end forms a radially inwardly open angularly limited cutout and at least two axially spaced, angularly offset, and radially outwardly projecting stop bumps on the stem are axially displaceable through the cutout in respective angularly offset positions of the stem. The stop bumps are axially engageable against the structure except when the stem is in the respective angular position. An elastically deformable brake element engaged between the body and the stem for axially slowing axial forward advance of the stem.

U.S. Pat. No. 5,817,056 titled "Prefilled Syringe" discloses a prefilled syringe capable of separate storage of different substances before use. It includes a tubular body having an injection needle at one end and a plunger at the other end, and a partition slidable axially in the tubular body. The partition includes a front part and a rear part independent of each other, and as a whole dividing the interior space of the tubular body into a front compartment and a rear compartment in a sealing manner for storing mutually different substances. A bypass is disposed generally between the front and rear compartments to introduce the substance in the rear compartment into the front compartment when the partition is slid under pressure provided by the plunger to be adjacent to the bypass to thereby mix the substances immediately prior to injection.

U.S. Pat. No. 5,364,350 titled "Twin-Chamber Syringe Filled with a Charge of Activity-Sensitive Human Protein" discloses a twin-chamber syringe that has a pyrogen-free sterile solvent in the chamber averted from the needle, and in the second chamber facing the needle a charge of activity-sensitive human protein, introduced and lyophilized in a single operation in the syringe, where it is stored, in a quantity necessary for therapeutically effective administration. The invention also relates to the filling of the syringe and the potential it offers for immediate use of activity-sensitive human proteins and for self-administration at home.

U.S. Pat. No. 5,899,881 titled "Stopper Assembly Having Bypass Features for Use in a Multi-Chamber Syringe Barrel" discloses a stopper assembly having by-pass features for use in a multi-chamber syringe barrel. The stopper assembly includes a sequential stopper body responsive to fluid forces for enabling the sequential delivery of disparate contents, such as disparate fluids, separately held in the syringe barrel. The sequential stopper body has a generally cylindrical sidewall with a distal end, a proximal end and a longitudinal axis therethrough. The stopper assembly also includes a generally cylindrical flow channelizer mounted to the distal end of the sequential stopper body. The flow channelizer enables the reconstitution of dry medicament held in the syringe barrel distally of the flow channelizer. The flow channelizer features opposed proximal and distal ends and a generally cylindrical outer surface therebetween. At least one fluid flow channel extends between the proximal and distal ends of a flow channelizer. A distally directed, conically-shaped projection is located at the distal end of the flow channelizer to prevent the accumulation of dead space between the channelizer and the internal shoulder located at the distal end of the syringe barrel. The stopper assembly may be employed in a multi-chambered syringe barrel featuring a by-pass channel to permit fluids to pass distally of the stopper assembly. The multi-barreled syringe barrel can be separated into disparate chambers by one or more by-pass stoppers so as to contain disparate components intended for sequential delivery by the stopper assembly.

U.S. Pat. No. 7,021,561 titled "Spray Device and Method" discloses a spray device including a barrel having a bypass and at least two spaced stoppers defining a first and second chambers and a spray nozzle. Movement of the first stopper drives the second stopper to the bypass and the fluid in the first chamber into the second chamber, mixing the fluid and substance. Continued movement of the first and second stoppers drives the mixture through the spray nozzle. The spray device may include a third stopper having a body in the tubular barrel which is moved toward the spray nozzle. The movement of the third stopper provides space for the mixture and prevents unpressurized fluid from flowing through the spray nozzle. The third stopper includes an axial stalk. The stalk may be deformable or the stalk may be separate from the body and the spray nozzle includes a longitudinal internal passage which provides communication with the spray port.

U.S. Pat. No. 4,036,225 titled "Bicompartmental Syringe" discloses a syringe for use in the distribution, conditioning and injection of two or more products to be mixed just before use, characterized in that it comprises two separate and contiguous compartments A and B, resulting from the assembly of two complimentary, joinable receptacles.

U.S. Pat. No. 4,613,326 titled "Two-Component Medication Syringe Assembly" discloses a two-component syringe assembly which includes an elongate barrel having a chamber for retaining fluid and a distal end having a passageway therethrough communicating with the chamber. A bypass stopper is slidably positioned in fluid-tight engagement inside the barrel. The barrel also includes a bypass defining a bypass zone positioned along the barrel for allowing fluid to flow around the bypass stopper when the bypass stopper is positioned intermediate the ends of the barrel in the bypass zone. A stopper is slidably positioned in fluid-tight engagement inside the barrel. A rigid plunger rod having an elongate body portion engages the stopper to facilitate its operation. A barrier flange is positioned on the body portion and intermediate the ends thereof. The barrier flange projects outwardly from the body portion into the space between the inside wall of the barrel and the outside of the body portion for acting as a barrier for blocking the path of fluid which may be propelled in a distal direction through the bypass when the syringe is being operated. The area described by the barrier flange as viewed along the longitudinal axis of the plunger rod is at least about 87 percent as large as the area described by the interior of the barrel as viewed along the longitudinal axis of the barrel.

PCT Publication No. WO2006/003653 titled "A Syringe Assembly" discloses a syringe assembly that consists of two basic types of assembly units: a dispensing unit, and a separate, independent plunger unit. The dispensing unit and the plunger unit are assembled together coaxially to form a two-unit syringe assembly for storage or prior to use. At least the dispensing unit is a container for a material to be dispensed and, by inserting one or more extension units between the dispensing unit and the plunger unit, additional compartments may be added. Each extension unit may contain a different component of a formulation in any predetermined quantity. The syringe assembly allows the user to store one or more components of a formulation in separate individual units that can be assembled easily into a single multi-compartment syringe assembly, which can store the multiple components separately until they are ready for use, at which time the components may be mixed to form the formulation.

U.S. Pat. No. 4,424,057 titled "Wet-Dry Syringe" discloses a wet-dry syringe for combining and mixing a liquid and a solid medicament or at least two dissimilar liquid medicaments prior to the application thereof to a patient includes a first vial having liquid or solid medicament disposed between a pair of identical vial seals. A second vial functions as a piston rod and includes a pair of end seals with a liquid medicament disposed therein. One of the second vial seals includes a hollow piercing needle which when utilized to pierce one end seal of the first vial causes the medicament therein to flow into the first vial thereby mixing the medicaments prior to application to a patient by means of a needle piercing assembly which pierces the second of the first vial seals and the patient to which the mixed medicaments are to be infused. The second vial functions as a piston rod and aides in the discharge of the medicaments.

U.S. Pat. No. 5,704,918 titled "Syringe" discloses that in medical scenes requiring emergency, where plural medicines are to be injected simultaneously, or solution of solid medicine is to be injected, different kinds of injection agents, without being previously mixed, are accommodated in chambers formed separately in a cylinder. In using a syringe, both injection agents can be sequentially injected separately or together by a simple operation.

U.S. Pat. No. 7,731,678 titled "Syringe Devices and Methods for Mixing and Administering Medication" discloses a device having a chamber within a syringe. A fluid passageway extends through a syringe piston. A valve is associated with the passageway controlling fluid passage through the piston. The invention includes a piercing structure having a head segment and a body portion, with a channel through the body portion and through at least one surface of the head without passing through the tip. In another aspect the invention encompasses a method of preparing an agent for administration to an individual. A first component is provided within a syringe and a second component is provided within a vial. A closed valve is associated with a fluid passageway between the vial and the syringe barrel through a piston. Valve repositioning allows fluid passage and sliding of the piston joins the first and second components. Repeated sliding of the piston mixes the components to produce the medication agent.

PCT Publication No. WO 2003/084840 titled "Device for Dispensing a Fluid Product" discloses a device for dispensing a fluid product containing two separate fluid or powdery products which are mixed before being dispensed. Said device comprises a first reservoir containing a first fluid or powdery product, a second reservoir containing a second fluid or powdery product, a mixing system, and a dispensing system. The inventive device is characterized by the fact that the mixing system is provided with a piston which separates the first and second reservoirs and comprises one-directional valve means which release the product that is contained in the first reservoir towards the second reservoir and prevent the product that is contained in the second reservoir from flowing towards the first reservoir. Said separating piston is movable so as to increase the volume of the second reservoir when the mixing system transfers the first product contained in the first reservoir into the second reservoir, preventing any relief in the second reservoir during mixing.

U.S. Pat. No. 3,511,239 titled "Multi-Chamber Syringe" discloses a syringe, which comprises a vial cylinder and a piston axially movable in the vial cylinder and dividing the vial cylinder into at least two separate chambers. The piston has means permitting liquid movement from a front to a rear chamber but blocking movement of said liquid in the opposite direction. A piston rod is non-movably secured to and displaces the piston, which is movable in the vial cylinder towards the injection end thereof. At least one stopper has a central bore and is disposed in and seals the vial cylinder, permitting independent and free movement of the piston during its forward movement, and the piston rod projects through and is guided by the stopper.

U.S. Pat. No. 3,662,753 titled "Syringe" discloses a syringe assembly enabling mixed discharge of substances retained in separated condition until intended use, employing a plunger and barrel arrangement that retains the substances separated during storage, allows mixing thereof prior to discharge, and causes discharge of the mixed substances. The plunger head has a diagonally oriented peripheral seal lip, preferably cooperative with differing diameter barrel portions.

European Patent publication No. 242,956 titled "Self-Contained Material Mixing Apparatus" discloses a self-contained material mixing apparatus that is useful for mixing two substances separately contained in the apparatus. The apparatus is embodied as a syringe having a piston therein separating two compartments within the syringe body. The piston causes an incompressible substance in the rearward compartment to pass to the forward compartment when the volume of the rearward compartment is reduced, but precludes passage of substances in the forward compartment to the rearward compartment. The substances to be ultimately mixed together are separately placed in the compartments, which substances can be, for example, a drug and a diluent. For mixing of the substances, the piston is moved rearwardly in the syringe and to produce an incompressible material in the rearward compartment that is forced to the front compartment through the one-way valve provided by the piston. After mixing of the substances in the forward compartment, the material is discharged from the syringe to a patient by moving the piston forwardly in the syringe to expel the mixture from the syringe through an outlet nozzle located at the front of the syringe.

U.S. Pat. No. 3,766,917 titled "Two Compartment Ampul Syringe" discloses a two-chamber syringe with an ampoule cylinder which at one end runs into a mouthpiece, designed to take an injection needle and which is as a rule closed in the first place, with at the end of the ampoule cylinder opposite the mouthpiece an elastic closure piston which seals against the exterior, and with a separating piston which divides the ampoule cylinder into two chambers, and with at least one pusher element acting on the separating piston, characterized in that the separating piston and/or an associated pusher element, passing through the separating piston and displaceable, has or forms a connection channel bridging over the separating piston, which channel prior to use of the syringe ampoule is closed, and can be opened by an axial movement of the pusher element relatively to the separating piston, and in that both pistons are made displaceable, and during the injection can be connected together so as to be displaceable in common.

PCT Publication No. WO 2008/150208 titled "A Substance Dispensing Device and a Filling Instrument for such a Device" discloses a device for storing, mixing and dosing of substances, typically used as a syringe. The device comprises a cylinder with a spout, an end piston and at least one mixing piston. At least a first and a second cylinder volume separated by the mixing piston are formed, The mixing piston is provided with a valve device which, when open, allows substance to be exchanged between said first and second cylinder volumes, and where the mixing piston is slideable with respect to the end piston for mixing of substances between the first and second cylinder volumes. Such a device may store two or more substances completely sealed and separate from each other. The device further allows mixing of selected substances inside a sterile device that may be used as a syringe. Finally, the same device also allows sequential dispensing of substances, or mixes of substances. The invention further relates to a filling instrument for such a device for storing, mixing and dosing of substances.

U.S. Pat. No. 5,785,683 titled "Disposable Syringe with Two Variable Volume Chambers" discloses a pre-filled disposable syringe to be used in the administration of powdered drug diluted at the time of injection.

U.S. Patent Publication No. 2011/0155620 titled "Rapid Reconstitution for Lyophilized Pharmaceutical Suspensions" discloses a method of preparing and reconstituting a sterile, lyophilized pharmaceutical active for rapid reconstitution by evacuating a lyophilized pharmaceutical active-containing container until the pressure within the container is less than about 300 Torr and hermetically sealing the evacuated container. The sterile, lyophilized pharmaceutical active can be prepared by flash freezing a pharmaceutical active-containing composition then lyophilizing the composition. The hermetically sealed lyophilized pharmaceutical active can be reconstituted by adding at least the total volume of liquid necessary for reconstitution of the sterile, lyophilized pharmaceutical active to the sterile, lyophilized pharmaceutical active, sealed under a pressure of less than about 300 Torr, in less than about 10 seconds to yield, within about 5 minutes, an administrable pharmaceutical active-containing composition. One aspect of the herein described sterile, lyophilized pharmaceutical active is a packaged sterile pharmaceutical active comprising an evacuated, hermetically sealed container having disposed therein a sterile, lyophilized pharmaceutical active, sealed under a pressure of less than about 300 Torr.

None of the references provide, in a single syringe, for the capability of vigorous back and forth mixing between the compartments and thus for rapid effective reconstitution and mixing of segregatedly stored components. The known systems utilizing valves are complex and can plug up with the mixing materials, or can leak during storage. Only uni-directional movement of the plunger (i.e. forward) is possible, resulting in insufficiently efficient mixing of the components. It would be desirable to develop alternative multi-compartment medical devices for segregated storage and on demand mixing of at least two components and for expressing the resulting mixture from the device for use in treating a patient.

SUMMARY OF THE INVENTION

In one aspect the invention encompasses a multi-compartment medical device or syringe for segregated storage and on demand mixing of at least two components and for expressing the resulting mixture from the device.

In one aspect the invention encompasses a medication agent preparation system comprising a multi-compartment syringe.

In another aspect the invention encompasses a method of preparing a medication agent for administration to an individual by mixing at least two components stored in segregation within the same device, and expressing the resulting mixture from the device for administration to an individual.

In yet another aspect of the invention, the device enables the user to move plunger back and forth for through and rapid mixing of separately stored components, and when mixing is accomplished, the device enables full expression of the mixed contents.

In one embodiment, the present invention is directed to a multi-compartment medical device for segregated storage and on demand mixing of at least two components and expression of a resulting mixture from the device having a tubular barrel that extends along an axis and has a front end and a rear end spaced axially behind the front end wherein the front end has an opening to express the mixture and a removable cap on said opening. A gasket seals the rear end of the tubular barrel and has an aperture. A plunger is located between the gasket and front end that is axially slidable within the tubular barrel and subdivides the tubular barrel into a front compartment between the plunger and the opening and a rear compartment that is between the plunger and the gasket. A stem is attached to the plunger and projects axially rearward out of the rear end through the gasket to sealing the aperture and be axially slidable through the gasket aperture. The device further includes at least one bypass in the barrel that is positioned between the front end and the rear end of the tubular barrel so as to enable fluid movement of the components between the front compartment and rear compartment. The plunger and the rear compartment are located axially behind the front compartment. The front end compartment can be partially filled with a first component, while said rear compartment can be at least partially filled with a second component, and wherein at least one of the components is preferably a fluid. The bypass can be positioned in front of the plunger in the front compartment and the length of the bypass can be less than the length of the front compartment. Preferably, the length of the bypass is from about 30 to about 60% of the length of the front compartment.

In another embodiment, the device also includes a rear bypass that is positioned between the plunger and the gasket and the length of the rear bypass is substantially equivalent to the length of the rear compartment. A gap is provided between the rear bypass and the bypass that is from about one half to about triple the thickness of the plunger.

In another embodiment, the device described above also includes a separator that is slidably positioned on the stem between the plunger and the gasket and subdivides the rear compartment into a rear subcompartment between the gasket and the separator and an intermediate compartment between the separator and the plunger. A rear bypass is provided between the gasket and the separator wherein the length of the rear bypass is substantially equivalent to the length of the rear subcompartment. Additionally, an intermediate bypass is provided between the plunger and the separator wherein the length of the intermediate bypass is substantially equivalent to the length of the intermediate compartment. An intermediate bypass gap that is between the intermediate bypass and the bypass is from about one half to about double the thickness of the separator. A bypass gap that is between the intermediate bypass and the rear bypass is from about one half to about triple the thickness of the plunger. The front end compartment is partially filled with a first component, the rear subcompartment is partially filled with a second component, and the intermediate compartment is at least partially filled with an intermediate component. At least one of the components is a fluid. The device can also provide barb means on the barrel that will immobilize the separator in proximity to the gasket. In the alternative, barb means can be provided on the stem to immobilize the separator in proximity to the plunger.

In another embodiment, the first component in the device is a lyophilized protein and the second component is a fluid for reconstitution. Substantially all of the first component is positioned in close proximity to the front end. A plunger separates the first component and the second component and is positioned in close proximity to the front end. A bypass is positioned in the rear compartment between the gasket and the plunger and the length of the bypass is less than the length of the rear compartment.

In another embodiment, a vacuum is generated in the front compartment and pressure is generated in the rear compartment by pulling the plunger towards the rear end. The resulting vacuum is measured from about 0.9 atmosphere to about 0.1 atmosphere. The second component can thereby flow through the bypass and contact the first component. The length of the bypass is from about 20% to about 80% of the length of the rear compartment.

The present invention is also directed to a method of separately storing and mixing of at least two components and then expressing a resulting mixture in the medical devices described herein by moving the plunger using the stem within the barrel towards the front end and then towards the back end or vice versa, repeating this step until the components are mixed, turning the medical device with the front end downwards, repeating the first step until the mixture moves into the front compartment, removing the cap from the opening on the front end of the tubular barrel and expressing the mixture through the opening by pushing the plunger towards the front end.

BRIEF DESCRIPTION OF THE DRAWINGS

FIG. 3 shows schematic cross-sectional views of an embodiment of the multi-compartment medical device of the present invention.

FIG. 4 shows schematic cross-sectional views of an embodiment of the multi-compartment medical device of the present invention.

FIG. 5 shows schematic cross-sectional views of an embodiment of the multi-compartment medical device of the present invention.

FIG. 6 shows schematic cross-sectional views of an embodiment of the multi-compartment medical device of the present invention.

FIG. 7 shows schematic cross-sectional views of an embodiment of the multi-compartment medical device of the present invention.

DETAILED DESCRIPTION OF THE INVENTION

Figure 1:
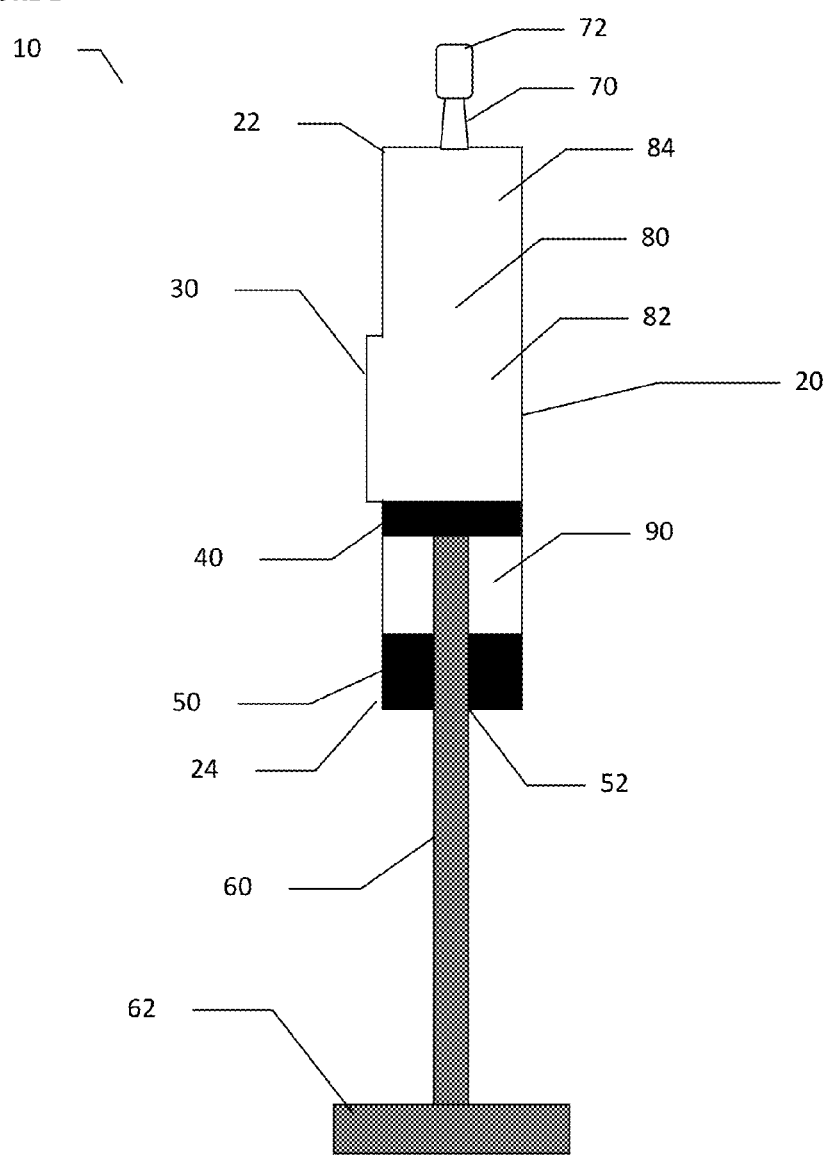
FIG. 1 shows schematic cross-sectional view of an embodiment of the multi-compartment medical device of the present invention.

Referring now to FIG. 1, a schematic cross-sectional view of an embodiment of the multi-compartment medical device 10 of the present invention is shown. The device 10 comprises a substantially tubular axially elongated glass or plastic barrel 20 slidably receiving a plunger 40. Barrel 20 has a front end 22 and a rear end 24 spaced axially behind the front end 22. Front end 22 is closed end of the barrel 20 and has a nozzle 70 through which the contents of the device 10 can be expressed or ejected. Nozzle 70 in other embodiments is exemplified by orifice, opening, spout, or luer connector, and is adapted for connecting to an optional delivery tube or needle or cannula or spray head (not shown). Nozzle 70 is capped by a removable cap 72, which can be attached via threads or frictionally attached. In some embodiments cap 72 is of snap-off or cut-off attachment type and cannot be re-attached after it is removed from nozzle 70.

A stem 60, which can be made of, for example, glass, plastic, or metal, is attached to and projects axially rearward from the plunger 40 through a gasket 50 which is installed at and seals rear end 24. Stem 60 has an optional handle 62 at the end of the stem that is adapted to facilitate moving of stem 60 with attached plunger 40 in and out of the barrel 20.

Gasket 50 has an aperture 52 adapted to slidably receive stem 60. Stem 60 is able to slidably move through aperture 52 while maintaining the seal of the rear end of barrel 20.

Figure 2:
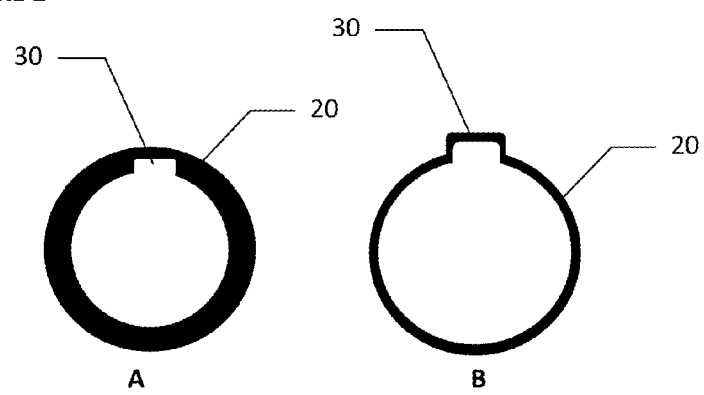
FIG. 2 shows schematic cross-sectional views of embodiments of the multi-compartment medical device of the present invention

Barrel 20 has a radially inwardly open and axially extending bypass 30. Referring now to FIG. 2, a cross-sectional view of barrel 20 is shown in the area of bypass 30, illustrating that bypass 30 is an axially extending groove in the wall of barrel 20 as shown in FIG. 2A or a an axially extending raised channel on the wall of the barrel 20 as shown in FIG. 2B, or a combination thereof. In all cases bypass 30 is inwardly open and outwardly closed axial channel on barrel 20.

Plunger 40, as shown in FIG. 1, subdivides barrel 20 into front compartment 80 and rear compartment 90 with the rear compartment 90 spaced axially behind the front compartment 80. Without reference to plunger 40, front compartment 80 is located between the most rearward edge (closest to rear end 24) of bypass 30 and front end 22. Front compartment 80 has front area 84 where no bypass 30 is present and bypass area 82 defined by the length of bypass 30. Plunger 40 maintains an air-tight or hermetic seal between compartments when not aligned along bypass 30.

The diameter of barrel 20 (excluding bypass 30) is from about 4 mm to about 50 mm, such as from 8 mm to 25 mm. The length of barrel 20 is from about 50 mm to about 300 mm, such as from 75 mm to 200 mm.

The dimensions of bypass 30 are, for rectangular bypass cross-section, from about 1×1 mm to about 4×4 mm, such as about 1×2 mm. In certain embodiments, the cross-sectional area of bypass is from 1% to about 10% of the cross-sectional area of barrel 20, such as from 2% to 5%. For a 15 mm internal diameter barrel 20, bypass 30 can be, for example, 1.5 mm×2 mm, or 2 mm×3 mm, i.e. about 1%-4% of the cross-sectional area of barrel 20. The length of bypass 30 is from about 5 mm to about 50 mm, such as 10 mm or 25 mm. The length of bypass 30 is from 20% to 80% of the length of the front compartment 80, such as 50% of the length of the front compartment 80.

The length of front compartment 80 and rear compartment 90 are from about 20 mm to about 150 mm. The length of front area 84 and bypass area 82 together equal to the length of front compartment 80. The volume of front area 84 is selected to accommodate all of mixture 150, i.e. the volume of front area 84 is approximately equal to sum of volumes of materials in bypass area 82 and in rear compartment 90. In one embodiment, the length of front area 84 is 30 mm, of bypass area 82 is 30 mm, and of rear compartment 90 is 30 mm. Thus for the internal diameter of the syringe equal to, for example, 18 mm, the volume of front area 84 is 7.6 mL, volume of bypass area 82 is 7.6 mL; and volume of rear compartment 90 is 7.6 mL. In another embodiment, the length of front area 84 is 50 mm, of bypass area 82 is 40 mm, and of rear compartment 90 is 30 mm. Thus for the internal diameter of the syringe equal to, for example, 18 mm, the volume of front area 84 is 12.7 mL, volume of bypass area 82 is 10.2 mL; and volume of rear compartment 90 is 7.6 mL. For the internal diameter of the syringe equal to, for example, 9 mm, the corresponding volumes will be one quarter of the volumes described above. In certain embodiments the length of front area 84 can range from 20 to 100 mm, of bypass area 82 can range from 20 to 100 mm, and of rear compartment 90 can range from 20 to 100 mm. In some embodiments, the lengths of these respective areas are as follows:

| Area of device 10 | Embodiment 1 Length, mm | Embodiment 2 Length, mm | Embodiment 3 Length, mm | Embodiment 4 Length, mm | Embodiment 5 Length, mm |
|---|---|---|---|---|---|
| front area 84 | 100 | 50 | 40 | 80 | 75 |
| bypass area 82 | 50 | 50 | 60 | 100 | 25 |
| rear compartment 90 | 20 | 50 | 40 | 60 | 25 |

The volume of front area 84 is selected to be at least equal to the volume of the final mixture of all components contained in device 10, or approximately equal or larger than the sum of volumes of components or agents contained in device 10.

The dimensions of aperture 52 closely correspond to dimensions of stem 60 to ensure slidable movement of stem 60 and a good seal between stem 60 and gasket 50. In case of cylindrical stem 60, aperture 50 is circular and has diameter from 90% to 100% of the outside diameter of stem 60, such as 99% of the outside diameter of stem 60. Typical diameters of stem 60 are 2-15 mm, such as 3 mm or 5 mm.

In the embodiment shown in FIG. 1, barrel 20 has a tubular or hollow cylinder shape with substantially circular cross-section. In other embodiments the cross-section can be non circular, such as oval, or rectangular.

Materials used in construction of the device 10 are typically biocompatible materials which are pharmacologically inert, sterilizable and nontoxic and are known in the art. Gasket 50 and plunger 40 are made of rubber-like compressible materials facilitating slidable sealing of barrel 20. Such materials are known in the art and include various types of rubber and silicone-based rubber or composite materials such as rubber, EPDM, nitrile, Buna, Neoprene, Aflas™, Kalrez™, Viton™, silicone, PTFE, urethane, ethylene propylene, etc. Barrel 20 and stem 60 are made of glass or generally inert plastics or polymers, known in the art, such as polypropylene, polyethylene, HDPE, PTFE, cyclic olefin copolymers, cyclic olefin polymers, etc.

Front compartment 80 is partially filled with a first component (not shown in FIG. 1) and rear compartment 90 is at least partially filled with a second component (not shown in FIG. 1), wherein at least one of the components is a fluid.

In one embodiment, front compartment 80 is partially filled with dry powder agent, such as lyophilized thrombin and rear compartment 90 is at least partially filled with reconstituting fluid, such as water, normal saline or calcium chloride solution, or with gelatin paste. In one embodiment, front compartment 80 is partially filled with reconstituting fluid such as water or with gelatin paste, and rear compartment 90 is at least partially filled with dry powder agent such as lyophilized thrombin. In one embodiment, front compartment 80 is partially filled with fluid such as normal saline or solvent, and rear compartment 90 is at least partially filled with concentrated liquid or paste, such as gelatin based paste or concentrated solution of agent such as lyophilized thrombin. In storage, plunger 40 seals, separates or segregates front compartment 80 from rear compartment 90.

Referring now to FIGS. 3(A-D), a schematic cross-sectional view of the embodiment shown in FIG. 1 is shown at different stages of mixing components and expressing the resulting mixture. FIG. 3A illustrates starting position or storage position whereby front compartment 80 is partially filled with a first component 100 and rear compartment 90 is at least partially filled with a second component 110, wherein at least one of the components is a fluid and the compartments separated, hermetically, from each other by plunger 40.

As illustrated in FIG. 3A, preferably first component 100 and second component 110 only partially fill correspondingly front compartment 80 and rear compartment 90. In certain embodiments, the volume of first component 100 is 20%; 50%; 75%; or 100% of the volume of bypass area 82. In certain embodiments, the volume of second component 110 is 20%; 50%; 75%; or 100% of the volume of rear compartment 90.

FIG. 3B illustrates that upon moving plunger 40 towards front end 22, first component 100 can freely move via bypass 30 from front compartment 80 into rear compartment 90 thus bringing first component 100 and second component 110 together for mixing.

FIG. 3C illustrates that upon moving plunger 40 towards rear end 24, a portion of partially mixed first component and second component, now forming mixture 150, is pushed by plunger 40 via bypass 30 back into front compartment 80. Although the figure shading of mixture 150 is suggestive of a homogenous, it is understood that the mixing step(s) can be incomplete, which can produce a mixture within the device that is not homogenous.

FIG. 3D illustrates that upon repeating the move of the plunger towards front end 22, mixture 150 moves via bypass 30 from front compartment 80 towards rear compartment 90 thus bringing portions of mixture 150 together for further mixing. Mixture 150 is preferably a homogenous mixture at the conclusion of this stage. As seen in FIGS. 3B and 3D plunger 40 can only move towards front end 22 until plunger 40 reaches front area 84. Once plunger 40 reaches front area 84, pressure buildup in front area 84 prevents plunger 40 from moving further towards front end 22, unless cap 72 is removed.

After repeating the moving of plunger 40 back and forth several times, i.e. from 2 to 20 times, such as 3 times or 5 times, a thorough mixing of components 100 and 110 is achieved, forming a homogenous mixture 150. During the moving of plunger back and forth, device 10 can be oriented with front end 22 facing upwardly, horizontally, or anywhere in between. In certain embodiments, device 10 during the mixing is oriented: substantially horizontally, such as horizontally ±30°; substantially vertically (as shown in FIGS. 1A-1D); with front end 22 facing upwardly ±90°; or at about 45° from horizontal orientation with front end 22 facing upwardly.

By orienting device 10 horizontally ±30° plunger 40 can be moved rearwards towards gasket 50 until it is substantially in contact with gasket 50, thus further facilitating and accelerating the formation of homogenous mixture 150.

Referring now to FIGS. 3(E-G), after mixing, front end 22 of device 10 is directed to face generally downwards (as shown in FIGS. 3E-3G), or with device 10 perpendicular to the ground ±45°.

Continuing to move plunger 40 back and forth several times, such as 1-5 or more times such as 2 or 10 times, results in mixture 150 moving through bypass 30 to front area 84, as illustrated in FIG. 3F. As further shown in FIG. 3G, once substantially all mixture 150 has moved into front area 84, plunger 40 is pushed towards front end 22 compressing mixture 150 in front area 84, with air pressure equilibrating via bypass 30, and sealing mixture 150 within front area 84. As can be seen from FIG. 3G, when further pressurized by plunger 40 moving towards front end 22, mixture 150 cannot move towards rear end 24 as bypass 30 is sealed by plunger 40. Thereafter removable cap 72 is removed from nozzle 70, and as shown in FIG. 3H, mixture 150 can be expressed from device 10 by plunger 40 via nozzle 70. During expression, device 10 can be oriented in any direction as an ordinary syringe, with front end 22 facing upwards, horizontally, downwards, or anywhere in between.

The volume of front area 84 is selected to be at least equal to the volume of mixture 150, or approximately equal or larger than the sum of volumes of components 100 and 110.

Thus device 10 enables separate sterile storage of components 100 and 110; thorough sterile mixing of these components to form mixture 150 in the same device 10, and sterile expression of mixture 150 from device 10 for biomedical application.

Referring now to FIG. 4(A-D), an embodiment of the device 10 of the present invention similar to previous embodiment, but having an additional rear bypass 35 is shown. As seen in FIG. 4A, rear bypass 35 starts at gasket 50 and extends over rear compartment 90 with distance between bypasses or bypass gap 38 between bypass 30 and rear bypass 35 having length of about 1-10 mm, more preferably about 2 mm-8 mm such as 5 mm. In one embodiment, bypass gap 38 has length that is from about one half to about triple the thickness of plunger 40. In one embodiment, bypass gap 38 has length that is equal to the thickness of plunger 40. In all embodiments, bypass gap 38 has length that is sufficient to accommodate the sealing positioning of plunger 40 at bypass gap 38 between rear compartment 90 and front compartment 80 fully separating components 100 and 110 during storage and prior to mixing, as shown in FIG. 4A.

When storing components 100 and 110 prior to mixing, plunger 40 maintains a seal between compartments as plunger 40 is positioned against bypass gap 38.

Similarly to the embodiments shown in FIGS. 1 and 3, the length of front area 84 can range from 20 to 100 mm, of bypass area 82 can range from 20 to 100 mm, and of rear compartment 90 can range from 20 to 100 mm. The volume of front area 84 is selected to be at least equal to the volume of mixture 150, or approximately equal or larger than the sum of volumes of components 100 and 110.

As indicated in FIGS. 4(A-D), for mixing components 100 and 110, plunger 40 can be moved towards front end 22 (FIG. 4B), and backwards towards rear end 24 (FIG. 4C), or in reverse order. As seen in FIGS. 4B and 4D plunger 40 can only move towards front end 22 until plunger 40 reaches front area 84. Once plunger 40 reaches front area 84, pressure buildup in front area 84 prevents plunger 40 from moving further towards front end 22.

As shown in FIG. 4C, plunger 40 moving backwards towards rear end 24 can move all the way back and reach gasket 50 thus enabling faster mixing of components 100 and 110 and formation of mixture 150, with component 110 or partially formed mixture 150 (as shown in FIG. 4C) moving via rear bypass 35 towards front compartment 80. FIG. 4D shows that plunger 40 can be continuously moved back and forth (with plunger 40 in the forward position in FIG. 4D) effecting further homogenization and thorough mixing of mixture 150 comprising components 100 and 110, with mixture 150 moving between front compartment 80 and rear compartment 90 via bypass 30 and rear bypass 35. When moving plunger 40 rearwards towards gasket 50 as shown in FIG. 4C, the preferred orientation of device 10 is with front end 22 facing substantially horizontally, such as horizontally ±30° or at about 45° from horizontal orientation with front end 22 facing upwardly, so as to enable the flow of fluid from rear compartment 90 towards front compartment 80.

As illustrated in FIG. 4A, preferably first component 100 and second component 110 only partially fill correspondingly front compartment 80 and rear compartment 90. In certain embodiments, the volume of first component 100 is 20%; 50%; 75%; or 100% of the volume of bypass area 82. In certain embodiments, the volume of second component 110 is 20%; 50%; 75%; or 100% of the volume of rear compartment 90.

After repeating the moving of plunger 40 back and forth several times, i.e. from 2 to 20 times, such as 3 times or 5 times, a thorough mixing of components 100 and 110 is achieved, forming a homogenous mixture 150. During mixing the orientation of device 10 is as described above for mixing stage.

Referring now to FIGS. 4(E-H), in preparation to expressing mixture 150, after mixing, device 10 is directed substantially downwards, with front end 22 facing downwards with device 10 perpendicular to the ground (as shown in FIGS. 4E-4H), or with device 10 perpendicular to the ground ±45°.

Continuing moving of plunger 40 back and forth several times, such as 1-5 or more times such as 2 or 10 times, results in mixture 150 moving through bypass 30 and rear bypass 35 to front area 84, as illustrated in FIG. 4F. As further shown in FIG. 4G, once substantially all mixture 150 has moved into front area 84, plunger 40 is pushed towards front end 22 compressing mixture 150 in front area 84, with air pressure equilibrating via bypass 30, and sealing mixture 150 within front area 84. As can be seen from FIG. 4G, when further pressurized by plunger 40 moving towards front end 22, mixture 150 cannot move towards rear end 24 as bypass 30 is sealed by plunger 40. Thereafter removable cap 72 is removed from nozzle 70, and as shown in FIG. 4H, mixture 150 can be expressed from device 10 by plunger 40 via nozzle 70. During expression, device 10 can be oriented in any direction as an ordinary syringe, with front end 22 facing upwards, horizontally, downwards, or anywhere in between.

Thus device 10 enables separate sterile storage of components 100 and 110; thorough sterile mixing of these components forming mixture 150 in the same device 10, and sterile expression of mixture 150 from device 10 for biomedical application.

Referring now to FIGS. 5(A-C), an embodiment of the device 10 of the present invention similar to previous embodiment, but having an additional intermediate bypass 36 is shown. As seen in FIG. 5A, intermediate bypass 36 is positioned between bypass 30 and rear bypass 35, with bypass gap 38 between rear bypass 35 and intermediate bypass 36 and intermediate bypass gap 39 between intermediate bypass 36 and bypass 30. The design of intermediate bypass 36 and intermediate bypass gap 39 is similar to described above for bypass 30 and bypass gap 38.

A separator 45 is slidably positioned on stem 60 between plunger 40 and gasket 50 and is subdividing rear compartment 90 into rear subcompartment 91 between gasket 50 and separator 45 and intermediate compartment 92 between separator 45 and plunger 40. Separator 45 has diameter fitting inside barrel 20 in slidable fit, and an aperture adapted to slidably receive stem 60. Separator 45 is able to slide on stem 60 within barrel 20 while maintaining tight fit against stem 60 and barrel 20. Separator 45 is initially positioned against bypass gap 38 between rear bypass 35 and intermediate bypass 36.

During storage, plunger 40 is positioned against intermediate bypass gap 39 thus separating and maintaining a seal between front compartment 80 and intermediate compartment 92. During storage, separator 45 is positioned against bypass gap 38 thus separating and maintaining a seal between intermediate compartment 92 and rear subcompartment 91.

Front compartment 80 contains first component 100; rear subcompartment 91 contains second component 110; intermediate compartment 92 contains intermediate component 112. At least one of first component 100; second component 110 and intermediate component 112 is a fluid, such as saline, water, paste or gel.

As illustrated in FIG. 5A, preferably first component 100, second component 110, and intermediate component 112 only partially fill correspondingly front compartment 80, rear subcompartment 91, and intermediate compartment 92. Volume of second component 110 in rear subcompartment 91 is selected so that there is enough of compressible gas phase in rear subcompartment 91 so that separator 45 can be moved rearwards into the area of bypass 35 enabling second component 110 to mix with first component 100, and intermediate component 112. In certain embodiments, the volume of second component 110 is 30%; 50%; or 75% of the volume of rear subcompartment 91. In certain embodiments, the volume of first component 100 is 30%; 50%; 75%; or 100% of the volume of bypass area 82. In certain embodiments, the volume of intermediate component 112 is 30%; 50%; 75%; or 100% of the volume of intermediate compartment 92. The length of front area 84 can range from 20 to 100 mm, of bypass area 82 can range from 20 to 100 mm, of intermediate compartment 92 can range from 20 to 100 mm and of rear subcompartment 91 can range from 20 to 100 mm. In one embodiment, length of front area 84 is 60 mm, of bypass area 82 is 30 mm, of intermediate compartment 92 is 30 mm, and of rear subcompartment 91 is 30 mm. The volume of front area 84 is selected to be at least equal to the volume of mixture 150, or approximately equal or larger than the sum of volumes of components 100; 110; and 112.

Similar to the previously described embodiments, for mixing components 100, 110, 112, and forming mixture 150, plunger 40 can be moved back and forth, i.e. towards front end 22, and backwards towards rear end 24. Upon moving plunger 40, when it comes in contact with separator 45, plunger 40 engages separator 45. Separator 45 then can be moved by plunger 40 rearward towards gasket 50.

As seen in FIGS. 5C and 5E plunger 40 can only move towards front end 22 until plunger 40 reaches front area 84. Once plunger 40 reaches front area 84, pressure buildup in front area 84 prevents plunger 40 from moving further towards front end 22.

In one embodiment, an optional plunger barb 220 shown in FIG. 5A is mounted on stem 60 in proximity to plunger 40, barb 220 engages separator 45 upon moving plunger 40 when plunger 40 comes in contact with separator 45 so that separator 45 becomes immobilized on stem 60 in proximity to plunger 40, and continues to move with plunger 40 and stem 60 thereafter, as shown in FIGS. 5D and 5E. In another embodiment, an optional barrel barb 200 mounted inside barrel 20 in proximity to gasket 50, as shown in FIG. 5A engages separator 45 so that separator 45 becomes immobilized inside barrel 20 in proximity to gasket 50, and does not move anymore with plunger 40 or stem 60 thereafter, as shown in FIGS. 5B and 5C. Optional barrel barb 200 or optional plunger barb 220 are represented by one or more bumps or protrusions which are sized to engage with the pliable material of separator 45 and to establish a mechanical engagement with separator 45. In certain embodiments barbs 200 or 220 are conically shaped bumps having base diameter of 1-3 mm and height of 0.3-2.0 mm. In one embodiment, there are 4 barrel barbs 200 located symmetrically around barrel 20, each of conical shape having base diameter of 1 mm and height of 0.5 mm. In another embodiment, there are 4 plunger barbs 220 located symmetrically around stem 40, each of conical shape having base diameter of 1 mm and height of 0.5 mm.

As shown in FIGS. 5(B-C), barrel barb 200 is mounted inside barrel 20 in proximity to gasket 50 engages separator 45 once plunger 40 is moved towards rear end 24 so that separator 45 becomes immobilized inside barrel 20 in proximity to gasket 50, and does not move anymore with plunger 40 or stem 60 thereafter. Plunger 40 can be continuously moved back and forth (with separator 45 immobilized by barrel barb 200 at rear end 24) effecting further homogenization and thorough mixing of mixture 150. When moving plunger 40 rearwards towards gasket 50 as shown in FIGS. 5B and 5D, the preferred orientation of device 10 is with front end 22 facing substantially horizontally, such as horizontally ±30° or at about 45° from horizontal orientation with front end 22 facing upwardly, so as to enable the flow of fluid from intermediate compartment 92 and rear subcompartment 91 towards front compartment 80.

As shown in FIGS. 5(D-E), plunger barb 220 is mounted on stem 60 in proximity to plunger 40. Once plunger 40 is moved towards rear end 24 separator 45 becomes immobilized on stem 60 in proximity to plunger 40 and continues to move with plunger 40 and stem 60 thereafter. FIGS. 5(A-E) illustrate the mixing of components 100, 110, 112, and forming mixture 150 with components moving via bypasses between compartments. After repeating the moving of plunger 40 back and forth several times, i.e. from 2 to 20 times, such as 3 times or 5 times, a thorough mixing of components is achieved, forming a homogenous mixture 150. During mixing the orientation of device 10 is as described above for mixing stage.

Similarly to embodiments described above, in preparation to expressing mixture 150, after mixing, device 10 is directed substantially downwards, with front end 22 facing downwards with device 10 perpendicular to the ground (as shown in FIGS. 4E-4G), or with device 10 perpendicular to the ground ±45°.

Continuing moving of plunger 40 back and forth several times, such as 1-5 or more times such as 2 or 10 times, results in mixture 150 moving through bypasses 30, 35, 36 to front area 84. As described previously, once substantially all mixture 150 has moved into front area 84, plunger 40 is pushed towards front end 22 compressing mixture 150 in front area 84, sealing mixture 150 within front area 84. Thereafter removable cap 72 is removed from nozzle 70, and mixture 150 can be expressed from device 10 by plunger 40 via nozzle 70. During expression, device 10 can be oriented in any direction as an ordinary syringe, with front end 22 facing upwards, horizontally, downwards, or anywhere in between.

Thus device 10 enables separate sterile storage of three components 100, 110, 112; thorough sterile mixing of these components forming mixture 150 in the same device 10, and sterile expression of mixture 150 from device 10 for biomedical application.

Referring now to FIG. 6, an embodiment similar to embodiments of FIG. 5 is presented, but having only two bypasses: rear bypass 35 and intermediate bypass 36. There is no bypass 30 in the shown embodiment.

During storage, plunger 40 is positioned sealing front area 84 thus separating and maintaining a seal between front area 84 and intermediate compartment 92. During storage, separator 45 is positioned against bypass gap 38 thus separating and maintaining a seal between intermediate compartment 92 and rear subcompartment 91. Front area 84 contains first component 100; rear subcompartment 91 contains second component 110; intermediate compartment 92 contains intermediate component 112. At least one of first component 100; second component 110 and intermediate component 112 is a fluid, such as saline, water, alcohol, or other solvent, paste and/or gel. Separator 45 is initially positioned against bypass gap 38 between rear bypass 35 and intermediate bypass 36.

As illustrated in FIG. 6A, preferably first component 100, second component 110, and intermediate component 112 only partially fill correspondingly front compartment 80, rear subcompartment 91, and intermediate compartment 92. Volume of second component 110 in rear subcompartment 91 and intermediate component 112 in intermediate compartment 92 is selected so that there is enough of compressible gas phase in rear subcompartment 91 and intermediate compartment 92 so that separator 45 and plunger 40 can be moved rearwards enabling mixing of components 110, 112, and 100. In certain embodiments, the volume of second component 110 is 30%; 50%; or 75% of the volume of rear subcompartment 91. In certain embodiments, the volume of first component 100 is 30%; or 50% of the volume of front area 84. In certain embodiments, the volume of intermediate component 112 is 30%; 50%; 75% of the volume of intermediate compartment 92.

Similar to the previously described embodiments, for mixing components 100, 110, 112, and forming mixture 150, plunger 40 can be moved backward and forward i.e. first backwards towards rear end 24 and then towards front end 22. Upon moving plunger 40, when it comes in contact with separator 45, plunger 40 engages separator 45. Separator 45 then can be moved by plunger 40 rearward towards gasket 50. In one embodiment, an optional plunger barb 220 mounted on stem 60 in proximity to plunger 40 engages separator 45 so that separator 45 becomes immobilized on stem 60 in proximity to plunger 40, and continues to move with plunger 40 and stem 60 thereafter. In another embodiment, an optional barrel barb 200 mounted inside barrel 20 in proximity to gasket 50 engages separator 45 so that separator 45 becomes immobilized inside barrel 20 in proximity to gasket 50, and does not move anymore with plunger 40 or stem 60 thereafter.

As shown in FIGS. 6(B-C), barrel barb 200, which is mounted inside barrel 20 in proximity to gasket 50, engages separator 45 once plunger 40 is moved towards rear end 24 so that separator 45 becomes immobilized inside barrel 20 in proximity to gasket 50, and does not move anymore with plunger 40 or stem 60 thereafter. Plunger 40 can be continuously moved back and forth (with separator 45 immobilized by barrel barb 200 at rear end 24) effecting further homogenization and thorough mixing of mixture 150.

As shown in FIGS. 6(D-E), plunger barb 220 is mounted on stem 60 in proximity to plunger 40. Once plunger 40 is moved towards rear end 24 separator 45 becomes immobilized on stem 60 in proximity to plunger 40 and continues to move with plunger 40 and stem 60 thereafter.

As seen in FIGS. 6A, 6C, and 6E, plunger 40 can only move towards front end 22 until plunger 40 reaches front area 84. Once plunger 40 reaches front area 84, pressure buildup in front area 84 prevents plunger 40 from moving further towards front end 22.

The length of front area 84 can range from 20 to 150 mm, of intermediate compartment 92 can range from 20 to 100 mm and of rear subcompartment 91 can range from 20 to 100 mm. In one embodiment, length of front area 84 is 80 mm, of intermediate compartment 92 is 30 mm, and of rear subcompartment 91 is 30 mm. The volume of front area 84 is selected to be at least equal to the volume of mixture 150, or approximately equal or larger than the sum of volumes of components 100; 110; and 112.

FIGS. 6(A-E) illustrate the mixing of components 100, 110, 112, and forming mixture 150 with components moving via bypasses between compartments. After repeating the moving of plunger 40 back and forth several times, i.e. from 2 to 20 times, such as 3 times or 5 times, a thorough mixing of components is achieved, forming a homogenous mixture 150. During mixing the orientation of device 10 is as described above for mixing stage. When moving plunger 40 rearwards towards gasket 50 as shown in FIGS. 6B and 6D, the preferred orientation of device 10 is with front end 22 facing substantially horizontally, such as horizontally ±30° or at about 45° from horizontal orientation with front end 22 facing upwardly, so as to enable the flow of fluid from rear compartment 90 towards front compartment 80.

Similarly to embodiments described above, in preparation to expressing mixture 150, after mixing, device 10 is directed substantially downwards, with front end 22 facing downwards with device 10 perpendicular to the ground (as shown in FIGS. 4E-4G), or with device 10 perpendicular to the ground ±45°.

Continuing moving of plunger 40 back and forth several times, such as 1-5 or more times such as 2 or 10 times, results in mixture 150 moving through bypasses 35, 36 to front area 84. As described previously, once substantially all mixture 150 has moved into front area 84, plunger 40 is pushed towards front end 22 compressing mixture 150 in front area 84, sealing mixture 150 within front area 84. Thereafter removable cap 72 is removed from nozzle 70, and mixture 150 can be expressed from device 10 by plunger 40 via nozzle 70. During expression, device 10 can be oriented in any direction as an ordinary syringe, with front end 22 facing upwards, horizontally, downwards, or anywhere in between.

Thus device 10 enables separate sterile storage of three components 100, 110, 112; thorough sterile mixing of these components forming mixture 150 in the same device 10, and sterile expression of mixture 150 from device 10 for biomedical application.

Embodiments of the present invention can further be utilized for reconstituting dry materials with liquids, such as lyophilized materials, e.g. lyophilized proteins reconstituting with saline or water. Specifically lyophilization under vacuum can be enabled by the embodiment of the current invention shown in FIG. 7.

Referring now to FIGS. 7(A-C), an embodiment of device 10 substantially similar to embodiment shown in FIGS. 1 and 3 is presented. Device 10 has one bypass 30, plunger 40 mounted on stem 60, and gasket 50. The different arrangement of first component 100 (lyophilized or other dry material) and second component 110 (liquid material) in the shown embodiment enables reconstitution under vacuum. As illustrated in FIG. 7A, initially plunger 40 is positioned in the proximity to front end 22, with first component 100 confined in a narrow area 300 between plunger 40 and front end 22. The volume of area 300 is preferably as small as possible, only to enable the placement of first component 100. Second component 110 is positioned between gasket 50 and plunger 40.

With device 10 oriented horizontally or horizontally ±30° and with bypass 30 facing downwards, pulling on handle 62 and pulling plunger 40 towards rear end 24 results in forming vacuum from the initially atmospheric pressure in the growing area 300 between plunger 40 and front end 22 where first component 100 is confined and simultaneous pressurization of the area between plunger 40 and gasket 50 where liquid second component 110 is confined. The movement of plunger 40 towards rear end 24 is made possible by incomplete fill of the space between plunger 40 and gasket 50 with second component 110, leaving gas phase between plunger 40 and gasket 50. Vacuum will increase as plunger 40 moves towards rear end 24 until plunger 40 reaches bypass 30, as shown in FIG. 7B. The pressure in the area 300 will be from about 0.9 atmosphere to about 0.1 atmosphere (with numbers below 1 atmosphere corresponding to below atmospheric pressure i.e. vacuum), depending on the ratio of volume of the area 300 between plunger 40 and front end 22 in the initial state prior to pulling plunger 40 towards rear end 24 and volume of the area 300 as plunger 40 reaches bypass 30. The pressure that is simultaneously generated in the area between plunger 40 and gasket 50 will be from about 1.05 atmosphere to about 3 atmosphere, such as 1.5 atmosphere, depending on the ratio between initial volume between plunger 40 and gasket 50 to the volume as plunger 40 reaches bypass 30 and also depending on the level of fill, i.e. the amount of gas relative to the amount of fluid in the area between plunger 40 and gasket 50. If the initial volume ratio to volume when plunger 40 reaches bypass 30 is about 3:2 and liquid fill is about 50% of the initial volume, the pressure will reach about 2 atmospheres. Referring to FIG. 7C, as plunger 40 goes over bypass 30, liquid second component 110 is driven by vacuum in area 300 between plunger 40 and front end 22 and by pressure in the area between plunger 40 and gasket 50 via bypass 30 towards front end 22, resulting in liquid second component 110 rapidly coming into contact with first component 100 under vacuum. Rapid reconstitution will then occur, with optional movements of plunger 40 back and forth over bypass 30 resulting in thorough mixing and reconstitution of first component 100 and liquid second component 110 forming mixture 150. Once the liquid second component 110 at least partially moved via bypass 30 towards front end 22, the pressure and vacuum in the device 10 will equilibrate back to atmospheric pressure.

After reconstituting under vacuum as described above and optional mixing, the expression from device 10 is performed as described above for embodiments shown in FIG. 3. Referring now to FIGS. 3E-3G, after mixing, device 10 is directed substantially downwards, with front end 22 facing downwards with device 10 perpendicular to the ground (as shown in FIGS. 3E-3G), or with device 10 perpendicular to the ground ±45°.

Continuing to move plunger 40 back and forth several times, such as 1-5 or more times such as 2 or 10 times, results in mixture 150 moving through bypass 30 to front area 84, as illustrated in FIG. 3F. As further shown in FIG. 3G, once substantially all mixture 150 has moved into front area 84, plunger 40 is pushed towards front end 22 compressing mixture 150 in front area 84, with air pressure equilibrating via bypass 30, and sealing mixture 150 within front area 84. As can be seen from FIG. 3G, when further pressurized by plunger 40 moving towards front end 22, mixture 150 cannot move towards rear end 24 as bypass 30 is sealed by plunger 40. Thereafter removable cap 72 is removed from nozzle 70, and as shown in FIG. 3H, mixture 150 can be expressed from device 10 by plunger 40 via nozzle 70. During expression, device 10 can be oriented in any direction as an ordinary syringe, with front end 22 facing upwards, horizontally, downwards, or anywhere in between.

Thus device 10 enables separate sterile storage of components 100 and 110; reconstitution under vacuum; thorough sterile mixing of these components forming mixture 150 in the same device 10, and sterile expression of mixture 150 from device 10 for biomedical application.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. A multi-compartment medical device for segregated storage and on demand mixing of at least two components and expression of a resulting mixture from the device, comprising:
   a) a tubular barrel extending along an axis and having a front end and a rear end spaced axially behind the front end wherein the front end has an opening to express the mixture and a removable cap on said opening;
   b) a gasket sealing the rear end of the tubular barrel and having an aperture;

c) a plunger located between the gasket and front end that is axially slidable within the tubular barrel that subdivides the tubular barrel into a front compartment between the plunger and the opening and a rear compartment between the plunger and the gasket;

d) a stem attached to the plunger and projecting axially rearward out of the rear end through the gasket, said stem sealing the aperture and axially slidable through the gasket aperture while maintaining the seal, with the dimensions of the aperture closely corresponding to dimensions of the stem; and e) at least one bypass in the barrel that is positioned between the front end and the rear end of the tubular barrel so as to enable fluid movement of the components between the front compartment and rear compartment; wherein the plunger and the rear compartment are located axially behind the front compartment, wherein said front compartment is partially filled with a first component and said rear compartment is at least partially filled with a second component, and wherein at least one of the components is a fluid, wherein the first component is a lyophilized protein, the second component is a fluid for reconstitution, substantially all the first component is positioned substantially in close proximity to the front end; the plunger separates the first component and the second component and is positioned in close proximity to the front end; the bypass is positioned in the rear compartment between the gasket and the plunger; and the length of the bypass is less than the length of the rear compartment, wherein a vacuum is generated in the front compartment and pressure is generated in the rear compartment upon pulling the plunger towards the rear end, with the device oriented horizontally or horizontally ±30° and with the bypass facing downwards, said vacuum being from about 0.9 atmosphere to about 0.1 atmosphere; wherein the second component flows through the bypass and contacts the first component; and wherein the length of the bypass is from about 20% to about 80% of the length of the rear compartment.

2. A method of separately storing and mixing of at least two components and then expressing a resulting mixture from a medical device according to claim 1 comprising: (a) Moving the plunger using the stem within the barrel towards the back end with the device oriented horizontally or horizontally ±30° and with the bypass facing downwards, thus forming vacuum in the front compartment; (b) Allowing the second component to move through the bypass into the front compartment and to mix with the first component; (c) Optionally moving the plunger within the barrel towards the front end and then towards the back end or vice versa; (d) Optionally repeating step (c) until the components are mixed; (e) Turning the medical device with the front end downwards with the device perpendicular to the ground ±45° (f) Repeating step (c) until the mixture moves into the front compartment; (g) Removing the cap from the opening on the front end of tubular barrel; (h) Expressing the mixture through the opening by pushing the plunger towards the front end.

* * * * *